(12) United States Patent
Abolmaesumi et al.

(10) Patent No.: US 11,131,650 B2
(45) Date of Patent: Sep. 28, 2021

(54) ULTRASONIC ANALYSIS OF A SUBJECT

(71) Applicants: THE UNIVERSITY OF BRITISH COLUMBIA, Vancouver (CA); QUEEN'S UNIVERSITY AT KINGSTON, Kingston (CA)

(72) Inventors: Purang Abolmaesumi, Vancouver (CA); Parvin Mousavi, Kingston (CA)

(73) Assignees: The University of British Columbia, Vancouver (CA); Queen's University at Kingston, Kingston (CA)

( * ) Notice: Subject to any disclaimer, the term of this patent is extended or adjusted under 35 U.S.C. 154(b) by 0 days.

(21) Appl. No.: 17/206,002

(22) Filed: Mar. 18, 2021

(65) Prior Publication Data

US 2021/0208107 A1 Jul. 8, 2021

Related U.S. Application Data

(63) Continuation of application No. PCT/CA2019/051314, filed on Sep. 16, 2019.

(Continued)

(51) Int. Cl.
*G01N 29/12* (2006.01)
*G01N 29/46* (2006.01)
*G01N 29/42* (2006.01)

(52) U.S. Cl.
CPC ............. *G01N 29/12* (2013.01); *G01N 29/42* (2013.01); *G01N 29/46* (2013.01);
(Continued)

(58) Field of Classification Search
CPC ......... G01N 29/12; G01N 29/42; G01N 29/46
See application file for complete search history.

(56) References Cited

U.S. PATENT DOCUMENTS 6,728,567 B2    4/2004   Rather et al.
2006/0287596 A1* 12/2006  Johnson ................... A61B 8/14
                                                  600/437
(Continued)

FOREIGN PATENT DOCUMENTS

CA    2652742 A1   12/2007
EP    3239706 A1   11/2017
(Continued)

OTHER PUBLICATIONS

Canadian Intellectual Property Office, International Search Report and Written Opinion of the International Searching Authority, dated Nov. 18, 2019, in PCT/CA2019/051314 which is the international application which shares the same priority as this U.S. application.

(Continued)

*Primary Examiner* — Tarun Sinha
(74) *Attorney, Agent, or Firm* — Kolitch Romano LLP

(57) ABSTRACT

A method of facilitating ultrasonic analysis of a subject is provided. The method involves producing signals for causing a set of outgoing ultrasonic signals to be transmitted to the subject, wherein the set of outgoing ultrasonic signals is defined at least in part by a variable imaging parameter that varies over time in accordance with a variable imaging parameter function, the variable imaging parameter function represented or representable at least in part by a function characteristic, receiving signals representing a time dependent representation of the subject generated from a set of received ultrasonic signals scattered by the subject, determining at least one property representation of the subject based on the function characteristic and the time dependent representation of the subject, and producing signals representing the at least one property representation of the subject to facilitate analysis of the subject. Systems, non-transitory (Continued)

computer readable media, and other methods are also provided.

16 Claims, 15 Drawing Sheets

Related U.S. Application Data

(60) Provisional application No. 62/732,904, filed on Sep. 18, 2018.

(52) U.S. Cl.
CPC ............. *G01N 2291/015* (2013.01); *G01N 2291/0231* (2013.01); *G01N 2291/02818* (2013.01); *G01N 2291/101* (2013.01)

(56) References Cited

U.S. PATENT DOCUMENTS

| | | | |
|---|---|---|---|
| 2010/0063393 A1 | 3/2010 | Moradi et al. | |
| 2017/0032702 A1 | 2/2017 | Goksel et al. | |
| 2020/0049817 A1* | 2/2020 | Schmid | G01S 15/8979 |
| 2020/0345325 A1 | 11/2020 | Tahmasebi Maraghoosh et al. | |

FOREIGN PATENT DOCUMENTS

| | | |
|---|---|---|
| WO | 2016198990 A1 | 12/2016 |
| WO | 2017192603 A1 | 11/2017 |

OTHER PUBLICATIONS

Bayat, Sharareh, et al.; "Investigation of Physical Phenomena Underlying Temporal Enhanced Ultrasound as a New Diagnostic Imaging Technique: Theory and Simulations"; IEEE Transactions on Ultrasonics, Ferroelectrics and Frequency Control (TUFFC), 2017.
Degirmenci, Alperen, et al.; "High Dynamic Range Ultrasound Imaging"; Int J Comput Assist Radiol Surg. May 2018.
Jensen, Jorgen Arendt, et al.; "Synthetic Aperture Ultrasound Imaging"; Ultrasonics 44, 2006.
Kurz, Jochen H., et al., "Porosity Determination of Carbon Fiber Reinforced Plastics (CFRP) in Aviation Applications Using Ultrasound Without a Back Wall Echo," Proceedings of the 19th World Conference on Non-destructive Testing, 2016.
Ma, Manyou; "A Comparative Evaluation of Two Synthetic Transmit Aperture with Virtual Source Beamforming Methods in Biomedical Ultrasound", UBC thesis, Dec. 2015.
Mattausch, Oliver, et al., "Image-Based PSF Estimation for Ultrasound Training Simulation", Computer-Assisted Applications in Medicine Group, ETH Zurich, Switzerland 2016.
Mattausch, Oliver, et al., "Image-Based Reconstruction of Tissue Scatterers Using Beam Steering for Ultrasound Simulation", IEEE Transactions on Medical Imaging, vol. 37, No. 3, Mar. 2018.
Oelze, Michael L., et al.; "Review of Quantitative Ultrasound: Envelope Statistics and Backscatter Coefficient Imaging and Contributions to Diagnostic Ultrasound," IEEE TUFFC, 2016.
Roberts, Ronald A.; "Micro-crack Ultrasound Scattering in Anisotropic Composite Laminates"; The 39th Annual Review of Progress in Quantitative Nondestructive Evaluation, 2013.
Synnevag, J.F., et al.; "Adaptive Beamforming Applied to Medical Ultrasound Imaging," in IEEE Transactions on Ultrasonics, Ferroelectrics, and Frequency Control, vol. 54, No. 8, Aug. 2007.
Waller, Laura; "Computational Microscopy"; University of California, Berkeley, 2017.

* cited by examiner

Ultrasound instruction message

⋮

244～ D = 20000
246～ A = 5000
248～ f = 0.03125

242～ focusDistance = D + A*sin(2pi*f*i)

Image record

282 — Index no.
284 — Image

Anomaly range record

362 — Minimum        0
364 — Maximum      15000

Ultrasound instruction message

⋮

D = 20000
A = 5000
B = 5000
f1 = 0.03125
f2 = 0.025

402 ∼ focusDistance = D + A*sin(2pi*f1*i) + B*sin(2pi*f2*i)

Ultrasound instruction message

⋮

D2 = 5000000
B = 50000
f2 = 0.025

422 ~ centreFrequency = D2 + B*sin(2pi*f2*i)

Ultrasound instruction message

⋮

D1 = 20000
B = 5000
f2 = 0.02 focusDistance = D + B*sin(2pi*f2*i)

ULTRASONIC ANALYSIS OF A SUBJECT

CROSS REFERENCES

The following applications and materials are incorporated herein, in their entireties, for all purposes: U.S. Provisional Application No. 62/732,904 entitled "ULTRASONIC ANALYSIS OF A SUBJECT", filed on Sep. 18, 2018; and International Application No. PCT/CA2019/051314, entitled "ULTRASONIC ANALYSIS OF A SUBJECT", filed Sep. 16, 2019.

BACKGROUND

1. Field

Embodiments of this present disclosure relate to nondestructive testing and more particularly to nondestructive testing using ultrasonic analysis of a subject.

2. Description of Related Art

Nondestructive Testing ("NDT") may be used to analyze or characterize various subjects, such as, for example, materials, tissue, tools, devices, tissue/organs, or other subjects where damage to the subject is undesirable, but analysis of the subject is required. Some NDT techniques may involve using microscopy or analysis of a single ultrasound image. However, such known NDT techniques may be difficult to set up and perform and/or may not perform well in detecting or characterizing subtle properties of the subjects, such as, for example where a change in or loss of signal caused by the property may be negligible.

SUMMARY

In accordance with various embodiments, there is provided a method of facilitating ultrasonic analysis of a subject, the method involving producing signals for causing a set of outgoing ultrasonic signals to be transmitted to the subject, wherein the set of outgoing ultrasonic signals is defined at least in part by a variable imaging parameter that varies over time in accordance with a variable imaging parameter function, the variable imaging parameter function represented or representable at least in part by a function characteristic, receiving signals representing a time dependent representation of the subject generated from a set of received ultrasonic signals scattered by the subject, determining at least one property representation of the subject based on the function characteristic and the time dependent representation of the subject, and producing signals representing the at least one property representation of the subject to facilitate analysis of the subject.

The set of outgoing ultrasonic signals may be a temporally ordered set of outgoing ultrasonic signals and the variable imaging parameter may vary over the temporally ordered set of outgoing ultrasonic signals.

The set of outgoing ultrasonic signals may include at least one ultrasonic beam and producing the signals for causing the set of outgoing ultrasonic signals to be transmitted to the subject may involve producing signals for causing the at least one ultrasonic beam to be transmitted to the subject, the at least one ultrasonic beam defined at least in part by the variable imaging parameter.

The variable imaging parameter may be a focal depth of the at least one ultrasonic beam and producing the signals for causing the at least one ultrasonic beam to be transmitted to the subject may involve producing signals for causing the focal depth of the at least one ultrasonic beam to vary over time according to the variable imaging parameter function.

The variable imaging parameter function may include a periodic function that varies over time at an imaging parameter frequency and the function characteristic may include the imaging parameter frequency.

Determining the at least one property representation of the subject may involve applying a band-pass filter to the time dependent representation of the subject, the band-pass filter configured to pass the imaging parameter frequency.

Determining the at least one property representation of the subject may involve applying a discrete Fourier transform to the time dependent representation of the subject to determine one or more imaging parameter frequency components, each of the one or more imaging parameter frequency components associated with the imaging parameter frequency.

The method may involve, for each of the one or more imaging parameter frequency components, applying at least one anomaly criterion to the imaging parameter frequency component to determine whether the imaging parameter frequency component indicates presence of an anomaly in the subject.

Applying the at least one anomaly criterion may involve determining whether the imaging parameter frequency component is outside of a predetermined normal range.

Producing the signals representing the at least one property representation of the subject may involve producing signals for causing at least one display to display a representation of the subject including indicators identifying the one or more imaging parameter frequency components determined to be outside of the predetermined normal range.

Producing the signals representing the at least one property representation of the subject may involve producing signals for causing at least one display to display a representation of the one or more imaging parameter frequency components.

The periodic function may be a first periodic function and the imaging parameter frequency may be a first imaging parameter frequency. The variable imaging parameter function may include a second periodic function that varies over time at a second imaging parameter frequency, different from the first imaging parameter frequency such that the variable imaging parameter function is represented at least in part by the second imaging parameter frequency. Determining the at least one property representation of the subject based on the function characteristic and the time dependent representation of the subject may involve determining the at least one property representation of the subject based on the first imaging parameter frequency, the second imaging parameter frequency, and the time dependent representation of the subject.

The set of outgoing ultrasonic signals may be a first set of outgoing ultrasonic signals, the variable imaging parameter may be a first variable imaging parameter, the variable imaging parameter function may be a first variable imaging parameter function, and the function characteristic may be a first function characteristic. The method may involve producing signals for causing a second set of outgoing ultrasonic signals to be transmitted to the subject, wherein the second set of outgoing ultrasonic signals is defined at least in part by a second variable imaging parameter that varies over time in accordance with a second variable imaging parameter function, the second variable imaging parameter function represented at least in part by a second function characteristic, and receiving signals representing a second time dependent representation of the subject generated from a second set of received ultrasonic signals scattered by the subject. Determining the at least one property representation of the subject may involve determining the at least one property representation of the subject based on the first function characteristic, the second function characteristic, and the time dependent representation of the subject.

The subject may be a composite material.

In accordance with various embodiments, there is provided a system for facilitating ultrasonic analysis of a subject comprising at least one processor configured to perform any of the above methods.

In accordance with various embodiments, there is provided a non-transitory computer readable medium having stored thereon codes which when executed by at least one processor cause the at least one processor to perform any of the above methods.

Other aspects and features of embodiments of the present disclosure will become apparent to those ordinarily skilled in the art upon review of the following description of specific embodiments of the present disclosure in conjunction with the accompanying figures.

BRIEF DESCRIPTION OF THE DRAWINGS

In drawings which illustrate embodiments of the present disclosure,

FIG. 4 is a representation of an exemplary ultrasound instruction message that may be used in the system shown in FIG. 1 in accordance with various embodiments of the present disclosure;

FIG. 9 is a representation of an exemplary anomaly range record that may be used in the system shown in FIG. 1 in accordance with various embodiments of the present disclosure;

FIG. 12 is a representation of an exemplary ultrasound instruction message that may be used in the system shown in FIG. 1 in accordance with various embodiments of the present disclosure;

FIG. 13 is a representation of an exemplary ultrasound instruction message that may be used in the system shown in FIG. 1 in accordance with various embodiments of the present disclosure;

FIG. 14 is a representation of an exemplary ultrasound instruction message that may be used in the system shown in FIG. 1 in accordance with various embodiments of the present disclosure.

DETAILED DESCRIPTION

Figure 1:
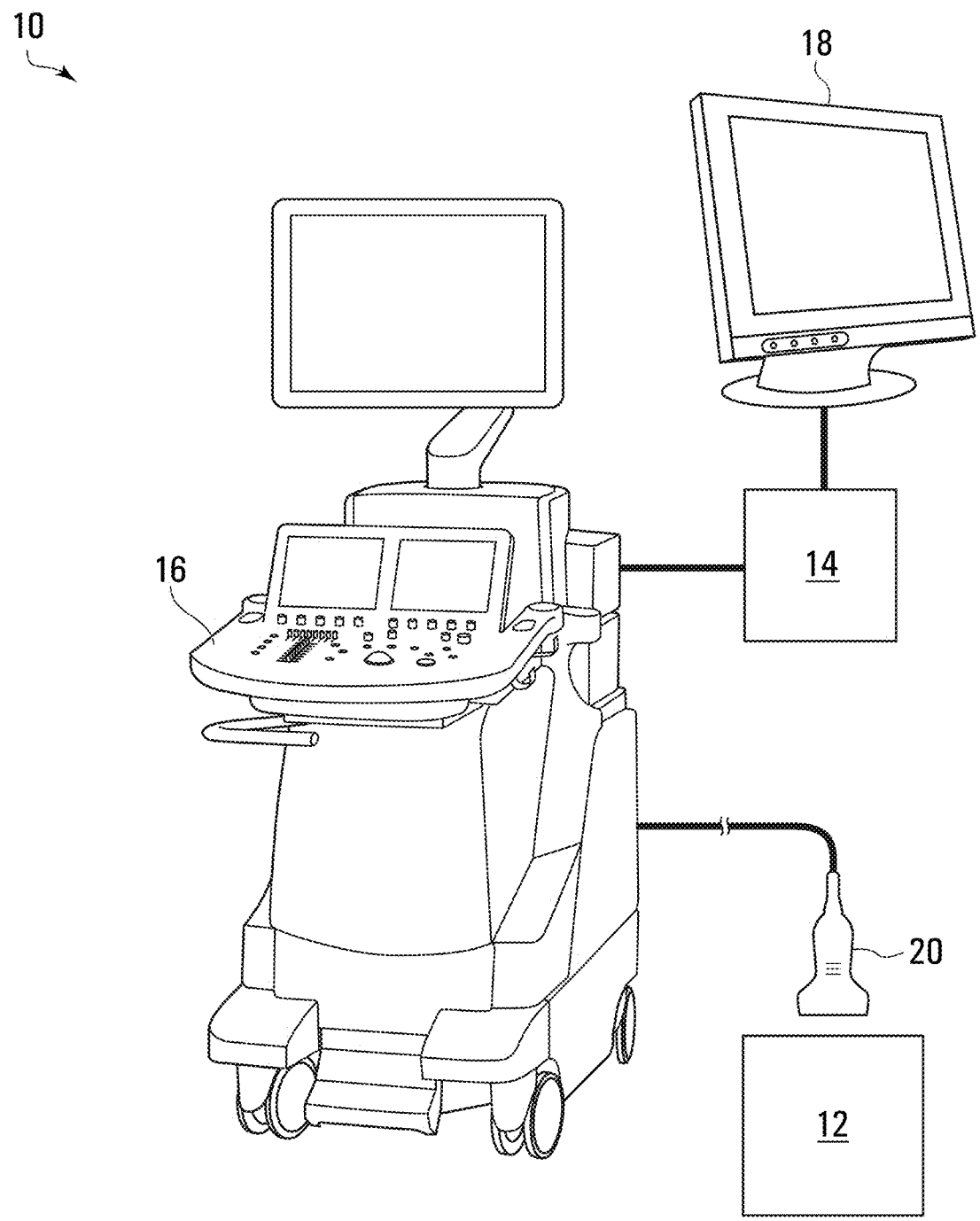
FIG. 1 is a schematic view of a system for facilitating ultrasonic analysis of a subject, according to various embodiments of the present disclosure.

Referring to FIG. 1, there is provided a schematic representation of a system 10 for facilitating ultrasonic analysis of a subject 12, in accordance with various embodiments described herein. The system includes a computer-implemented analyzer 14 and an ultrasound machine 16 in communication with the analyzer 14. In various embodiments, the system 10 may also include a display 18 in communication with the analyzer 14.

In some embodiments, the system 10 may facilitate ultrasonic analysis of materials or parts to allow detection of subtle defects in the materials, which may be difficult to detect using conventional NDT analysis. In some embodiments, the system 10 may facilitate ultrasonic analysis of advanced composite parts, such as parts made from fiber-reinforced composite materials, for example. In various embodiments, defects may include, for example, porosity, foreign object debris, impact-induced delamination, heat-induced resin degradation, and/or waviness of fibers or wrinkles in the fibers. In various embodiments, the system 10 may facilitate easier implementation of NDT without affecting workflow of a production factory and/or may provide improved detection of defects or properties of a subject, when compared to conventional NDT techniques.

In various embodiments, a user of the system 10 may initiate ultrasonic analysis of the subject 12 through interaction with the analyzer 14. For example, in some embodiments, the user may initiate ultrasonic analysis of the subject 12 during quality assurance testing of the subject 12. Upon initiation of the analysis, the analyzer 14 may be configured to produce signals for causing a set of outgoing ultrasonic signals to be transmitted to the subject 12, wherein the transmitted ultrasonic signals are defined at least in part by a variable imaging parameter that varies over time in accordance with a variable imaging parameter function and the variable imaging parameter function is represented or representable at least in part by a function characteristic. In various embodiments, the set of outgoing ultrasonic signals may be a temporally ordered set of outgoing ultrasonic signals and the variable imaging parameter may vary over the temporally ordered set of outgoing ultrasonic signals.

In various embodiments, varying at least one imaging parameter of the transmitted ultrasonic signals may result in a variation of the ultrasound point spread function used in the imaging system of the system 10. Backscattered RF data sensed for a point $x_0$ in the imaging system may be defined by the following equation:

$$I(x_0, t) = PSF(x_0) * s(x_0) + \frac{\partial PSF(x_0)}{\partial x} * s(x_0) A \sin(\omega t) + n$$

where $PSF(x_0)$ is an ultrasound point spread function at a point $x_0$ that is convolved with $s(x_0)$, the scattering function for the subject 12 at the same point, to generate $I(x_0, t)$, and n represents random noise, A is the amplitude of a micro vibration at point $x_0$ or the amplitude of variation in the ultrasound point spread function at point $x_0$, and $\omega$ is the frequency of variation in the ultrasound point spread function at point $x_0$.

Accordingly, knowledge of a function characteristic which may represent how the point spread function varies may be used to characterize or identify properties of the subject scattering function and therefore, may be used to characterize or identify properties of the subject 12.

In some embodiments, the variable imaging parameter that defines the transmitted ultrasonic signals may be a focal depth of the transmitted signals and the analyzer 14 may cause the ultrasound machine 16 to transmit ultrasonic signals to the subject 12, via a transducer 20 of the ultrasound machine, that have a focal depth that varies over time according to a variable imaging parameter function or focal depth function. In some embodiments, the focal depth function may be periodic at a focal depth variation frequency and this frequency may act as a function characteristic of the focal depth function. In various embodiments, the analyzer 14 may store the focal depth variation frequency for use later during analysis or characterization of the subject 12.

The ultrasound machine 16 may cause the transducer 20 to transmit, based on the signals received from the analyzer 14, a set of ultrasonic signals to the subject 12 and receive a set of reflected ultrasonic signals scattered by the subject. The ultrasound machine 16 may generate a time dependent representation of the subject 12 based on the received reflected ultrasonic signals and may send the time dependent representation to the analyzer 14. In some embodiments, the time dependent representation may include a temporally ordered set or sequence of image representations of the subject 12 representing the subject 12 over a time period. In some embodiments, this time dependent representation may be taken for a fixed location or volume in the subject 12, during that time period.

The analyzer 14 may receive signals representing the time dependent representation of the subject. For example, in some embodiments, the analyzer 14 may receive the sequence of image representations, from the ultrasound machine 16.

The analyzer 14 may then determine at least one property representation of the subject based on the function characteristic and the time dependent representation of the subject 12. In various embodiments, by basing the determination in part on the function characteristic, a representation of the subject 12 that would otherwise be difficult or impossible to discern may be determined. For example, in some embodiments, the time dependent imaging parameter function may be a periodic focal depth function and the analyzer 14 may use the frequency of the focal depth function as the function characteristic to generate one or more images, acting as property representations of the subject 12, based on the frequency of the focal depth function and the time dependent representation of the subject 12.

Figure 2:
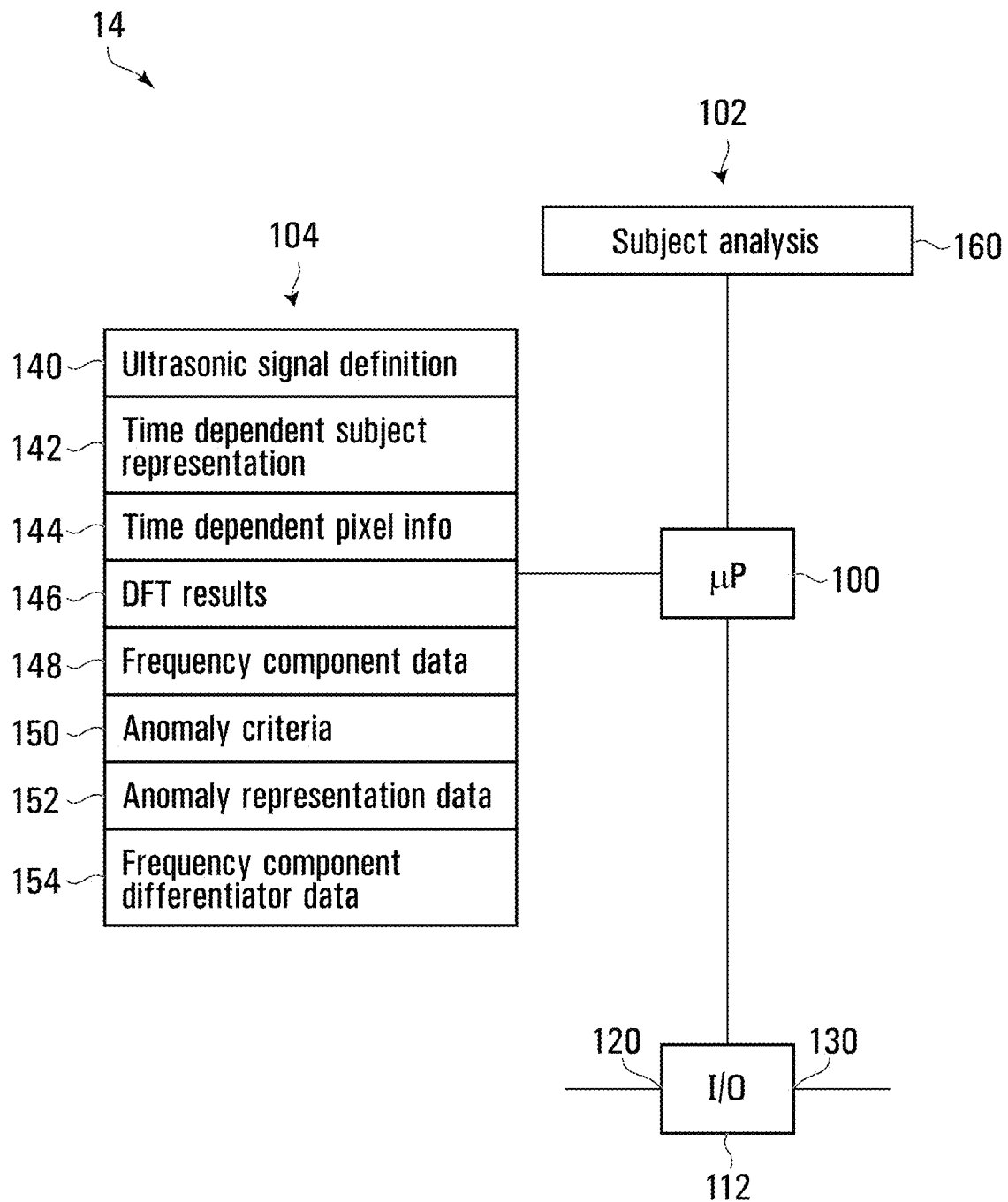
FIG. 2 is a schematic view of an analyzer of the system shown in FIG. 1 including a processor circuit in accordance with various embodiments of the present disclosure.

In some embodiments, determining the at least one property representation may involve applying a discrete Fourier transform (DFT) such as, for example, a fast Fourier transform, to the time dependent representation of the subject and choosing a component or filtering to determine the component of the result that corresponds to the frequency of the focal depth function. For example, in some embodiments, the time dependent representation of the subject may include a sequence of image representations of the subject as shown in FIG. 2, and the analyzer 14 may apply an FFT to each sequence of values for each pixel location. The analyzer 14 may then, for each pixel location, choose the FFT component that corresponds to the frequency of the focal depth function and set that component as an imaging parameter frequency component.

In various embodiments, determining the at least one property representation may involve the analyzer 14 generating an image representation of the determined imaging parameter frequency components. In some embodiments, determining the at least one property representation may involve the analyzer 14 applying at least one anomaly criterion to each of the determined imaging parameter frequency components to determine whether each respective one of the imaging parameter frequency components indicates presence of an anomaly in the subject 12.

The analyzer 14 may then produce signals representing the at least one property representation of the subject to facilitate analysis of the subject. In some embodiments, the analyzer may produce signals for causing the display 18 to display a representation of the image representation of the one or more imaging parameter frequency components and/or an image representation of the results of the application of the at least one anomaly criterion.

In various embodiments, varying an imaging parameter in the ultrasonic signal and knowing of a function characteristic of the variable imaging parameter may allow the analyzer 14 to derive properties of the subject 12 and provide analysis that otherwise would not be possible. In some embodiments, the properties may be derived by applying a function to the time dependent representation of the subject 12 wherein the function is defined by the function characteristic or is specific based on the function characteristic. In various embodiments, use of such a particularized property determining function may facilitate generating a representation of the subject 12 that makes properties of the subject 12 discernible, which would otherwise be difficult or impossible to discern using non-destructive testing.

Analyzer—Processor Circuit

Referring now to FIG. 2, a schematic view of the analyzer 14 of the system 10 shown in FIG. 1 according to various embodiments is shown. The analyzer 14 includes a processor circuit including an analyzer processor 100 and a program memory 102, a storage memory 104, and an input/output (I/O) interface 112, all of which are in communication with the analyzer processor 100. In various embodiments, the analyzer processor 100 may include one or more processing units, such as for example, a central processing unit (CPU), a graphical processing unit (GPU), and/or a field programmable gate array (FPGA). In some embodiments, any or all of the functionality of the analyzer 14 described herein may be implemented using one or more FPGAs.

The I/O interface 112 includes an interface 120 for communicating with the ultrasound machine 16 and an interface 130 for communicating with the display 18. In some embodiments, any of the interfaces 120 or 130 may facilitate wireless or wired communication. In some embodiments, the I/O interface 120 may include an ethernet interface for connecting to the ultrasound machine 16. In some embodiments, the I/O interface 130 may include an HDMI or another multimedia interface.

Referring to FIG. 2, in some embodiments, each of the interfaces may include one or more interfaces and/or some or all of the interfaces included in the I/O interface 112 may be implemented as combined interfaces or a single interface.

In some embodiments, where a device is described herein as receiving or sending information, it may be understood that the device receives signals representing the information via an interface of the device or produces signals representing the information and transmits the signals to the other device via an interface of the device.

Processor-executable program codes for directing the analyzer processor 100 to carry out various functions are stored in the program memory 102. Referring to FIG. 2, the program memory 102 includes a block of codes 160 for directing the analyzer 14 to perform subject analysis functions. In this specification, it may be stated that certain encoded entities such as applications or modules perform certain functions. Herein, when an application, module or encoded entity is described as taking an action, as part of, for example, a function or a method, it will be understood that at least one processor (e.g., the analyzer processor 100) is directed to take the action by way of programmable codes or processor-executable codes or instructions defining or forming part of the application.

The storage memory 104 includes a plurality of storage locations including location 140 for storing ultrasonic signal definition information, location 142 for storing time dependent representation of the subject 12 information, location 144 for storing pixel specific time dependent information, location 146 for storing discrete Fourier transform (DFT) result information, location 148 for storing frequency specific DFT component information, location 150 for storing anomaly criteria information, location 152 for storing anomaly representation data, and location 154 for storing frequency component differentiator data. In various embodiments, the plurality of storage locations may be stored in a database in the storage memory 104.

In various embodiments, the blocks of codes included in the program memory 102 may be integrated into a single block of codes and/or may include one or more blocks of code stored in one or more separate locations in program memory 102. In various embodiments, any or all of the locations in the storage memory 104 may be integrated and/or each may include one or more separate locations in the storage memory 104.

In various embodiments, each of the program memory 102 and/or the storage memory 104 may be implemented as one or more storage devices including, for example, random access memory (RAM), a hard disk drive (HDD), a solid-state drive (SSD), a network drive, flash memory, a memory stick or card, any other form of non-transitory computer-readable memory or storage medium, and/or a combination thereof. In some embodiments, the program memory 102, the storage memory 104, and/or any portion thereof may be included in a device separate from the analyzer 14 and in communication with the analyzer 14 via a network interface included in the I/O interface 112, for example.

Subject Analysis

Figure 3:
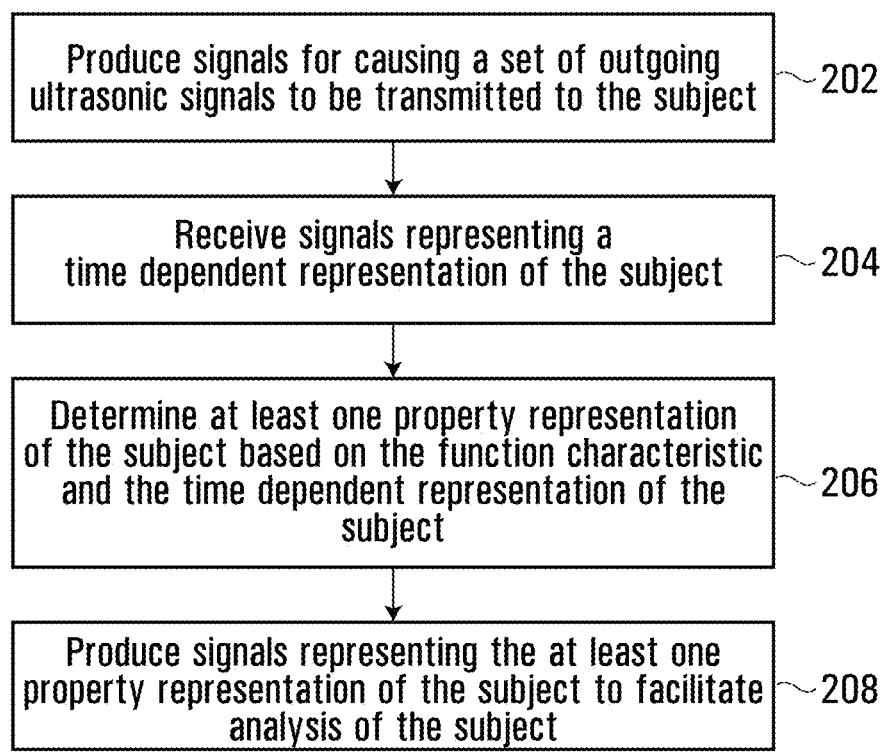
FIG. 3 is a flowchart depicting blocks of code for directing the analyzer of the system shown in FIG. 1 to perform subject analysis functions in accordance with various embodiments of the present disclosure.

Referring now to FIG. 3, a flowchart depicting blocks of code for directing the analyzer processor 100 shown in FIG. 2 to perform subject analysis functions in accordance with various embodiments is shown generally at 200. The blocks of code included in the flowchart 200 may be included in the block of codes 160 of the program memory 102 shown in FIG. 2, for example.

In some embodiments, execution of the flowchart 200 by the analyzer processor 100 may be initiated when a user or users of the analyzer 14 wishes to analyze or characterize the subject 12 or a similar subject, for example, to perform non-destructive testing. For example, in some embodiments, the display 18 shown in FIG. 1 may include a touch interface and the user may interact with the display 18 to initiate execution of the flowchart 200. In some embodiments, the results of the analysis may be used to determine whether the subject 12 is viable for use in an intended application and/or to determine the composition of the subject 12.

Referring to FIG. 1, in some embodiments, the subject 12 may be an advanced composite part, which may, for example, include a composite material having fibers and in some embodiments, the results of the analysis may be used to identify anomalies or defects, such as, for example, waviness of the fibers or wrinkles in the fibers, and thereby determine whether the subject 12 may be used in an aerospace application, for example. Accordingly, in various embodiments, the flowchart 200 may be initiated during quality assurance testing of the subject 12. In various embodiments, the subject 12 may be submerged in a water bath container on a table during analysis.

Referring to FIG. 3, the flowchart 200 begins with block 202 which directs the analyzer processor 100 to produce signals for causing a set of outgoing ultrasonic signals to be transmitted to the subject, wherein the set of outgoing ultrasonic signals are defined at least in part by a variable imaging parameter that varies over time in accordance with a variable imaging parameter function, the variable imaging parameter function represented or representable at least in part by a function characteristic. In some embodiments, the set of outgoing ultrasonic signals may be a temporally ordered set of outgoing ultrasonic signals and the variable imaging parameter may vary over the temporally ordered set of outgoing ultrasonic signals.

In some embodiments, the set of outgoing ultrasonic signals may include at least one ultrasonic beam and block 202 may direct the analyzer processor 100 to produce signals for causing the at least one ultrasonic beam to be transmitted to the subject, the at least one ultrasonic beam defined at least in part by the variable imaging parameter.

In some embodiments, the variable imaging parameter may be a focal depth and block 202 may direct the analyzer processor 100 to transmit to the ultrasound machine 16 shown in FIG. 1, an ultrasound instruction message, a portion of which is shown at 240 in FIG. 4, which may in some embodiments represent computer code, such as, for example C code, for directing the ultrasound machine to cause the transducer 20 to transmit ultrasonic signals to the subject such that the ultrasonic signals have a focal depth that varies over time according to a focal depth function. In various embodiments, the ultrasound machine 16 may include an ultrasound machine with a 1-D linear array transducer with 128 elements.

Referring to FIG. 4, in various embodiments, the ultrasound instruction message 240 includes a focal depth or focal distance function definition 242 that defines a focal depth or focal distance in microns as a function of an index number "i". The ultrasound machine 16 may be configured to transmit a temporally ordered set or sequence of ultrasonic signals indexed by the index number "i" to the subject 12 such that a sequence of images or frames having corresponding indices and representing the reflected or scattered signals can be generated. In some embodiments, the frame rate may be set at a frequency, such as for example, 730 frames per second, and the total number of ultrasonic signals or indices may be set to 128, for example. In various embodiments, a frame rate of about 730 frames per second may facilitate imaging the subject quickly in a short time period. In various embodiments, capturing 128 frames may allow later analysis, such as analysis using an FFT to be performed accurately.

Accordingly, in some embodiments, the focal depth function definition 242 being a function of i will result in the focal depth function being a function of time. Referring to FIG. 4, in various embodiments, the focal depth function definition 242 of the ultrasound instruction message 240 may represent the following function:

$$\text{Focal depth (in microns)} = D + A \sin(2\pi f \cdot i)$$

where i is the frame index number for each transmitted ultrasonic signal.

Referring still to FIG. 4, in various embodiments, the focal depth function definition 242 of the ultrasound instruction message 240 may be defined in part by respective values stored in a mean focal depth field 244, an amplitude field 246, and a focal depth frequency field 248 included in the ultrasound instruction message.

In various embodiments, the mean focal depth field 244 and the amplitude field 246 may have been previously set, for example, by a user of the analyzer 14. In some embodiments, the mean focal depth field 244 may be set to a depth that is in the center of the subject 12 being analyzed, which may facilitate more accurate characterization of the subject. In some embodiments, for example, the subject 12 may have a total depth of about 4 cm or 40000 microns and so the mean focal depth field 244 may have been previously set to 20000 microns.

In some embodiments, the imaging depth for imaging the subject 12 may be set such that a reasonably high resolution for imaging is achieved. For example, for a 5 MHz transducer, 4 cm depth may be reasonable. In some embodiments, lower than that like 1 cm, for example, may degrade beamforming quality and much higher than that like 10 cm, for example, may reduce the imaging resolution. In various embodiments, the subject 12 may be placed generally at the mean focal depth and in various embodiments, a typical focal depth may be about 1 cm to 3 cm for a 4 cm imaging depth.

The value of the focal depth frequency field 248 of the ultrasound instruction message 240 may have also been previously set, for example, by a user of the analyzer 14. In some embodiments, the focal depth frequency field 248 may be chosen such that the focal depth function definition 242 completes 1 period within a sample time period. For example, in some embodiments, a sample time period may include 128 frames, and so the focal depth frequency field 248 may be set to 1/128=0.03125. In various embodiments, based on the frame rate of 730 frames per second, this may result in a frequency of the focal depth function of about 5.7 Hz, hence with 128 frames, one cycle of the sinusoid may be sampled fairly densely and this may facilitate reliably reconstructing the amplitude of the sinusoid.

In various embodiments, the focal depth frequency field 248 may be set to a value such that each period is sampled at about 4 times the Nyquist rate given the imaging frame rate to facilitate reliable reconstruction of the signal in a noisy environment.

In some embodiments, the value stored in the focal depth frequency field 248 may act as an imaging parameter frequency and a function characteristic for the focal depth function defined by the focal depth function definition 242.

In some embodiments, the ultrasound instruction message 240 may have been previously stored in the location 140 of the storage memory 104 and block 202 may direct the analyzer processor 100 to retrieve the ultrasound instruction message 240 from the location 140 of the storage memory 104 and to send a representation of the ultrasound instruction message 240 to the ultrasound machine 16 via the interface 120 of the I/O interface 112 shown in FIG. 2.

After receiving the ultrasound instruction message 240 from the analyzer 14, the ultrasound machine 16 may cause the transducer 20 to transmit a plurality of outgoing ultrasonic signals to the subject based on the ultrasound instruction message 240. For example, in various embodiments, the ultrasound machine 16 may receive the ultrasound instruction message 240 shown in FIG. 4 and the ultrasound machine 16 may cause the transducer 20 to transmit 128 ultrasonic signals indexed from i=0 to i=127 at 730 signals/second and each defined at least in part by a focal depth determined according to the focal depth function definition 242 of the ultrasound instruction message 240. The transducer 20 then receives reflections of each of the transmitted ultrasonic signals from the subject 12 and the ultrasound machine 16 generates respective images, each representing a reflection of one of the transmitted signals and so corresponding to an index or frame number. For example, in some embodiments, the ultrasound machine 16 may generate 128 images indexed from i=0 to i=127 representing the subject 12 taken at 730 images/second representing reflections of the ultrasonic signals transmitted to the subject 12. In various embodiments, the ultrasound machine 16 may transmit the sequence of 128 images, each associated with a respective index number representing time, to the analyzer 14, for analysis.

Figure 5:
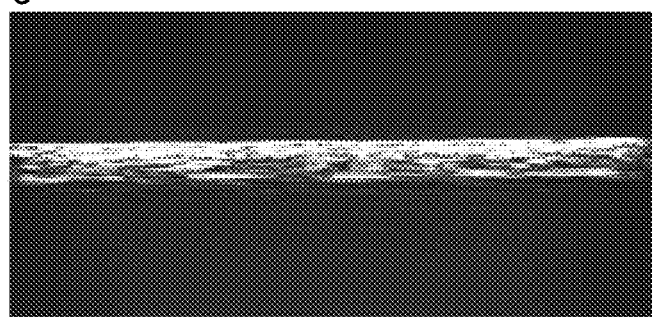
FIG. 5 is a representation of an exemplary image record that may be used in the system shown in FIG. 1 in accordance with various embodiments of the present disclosure.

For example, in various embodiments, the ultrasound machine 16 may generate and transmit to the analyzer 14 respective image records, an exemplary one of which is shown at 280 in FIG. 5. The image record 280 includes an index field 282 for storing an index value representing a time at which the image was taken and an image field 284 for storing an image representation of the reflected ultrasonic signals received at the transducer 20. In some embodiments, the image information stored in the image field 284 may include a plurality of pixel positions, each associated with a pixel value, wherein the pixel value represents an echo intensity which may represent a change in density, speed of sound and/or acoustic impedance of the subject at the pixel location. In some embodiments, the image information may represent an 8-12 bit image and the pixel values may each be within a range of 0-255 or 0-4095, for example.

Referring back to FIG. 3, block 204 directs the analyzer processor 100 to receive signals representing a time dependent representation of the subject generated from a set of received ultrasonic signal scattered by the subject. In some embodiments, block 204 may direct the analyzer processor 100 to receive a set of 128 image records, each having the same format as the image record 280 shown in FIG. 5, from the ultrasound machine 16 via the interface 120 of the I/O interface 112 shown in FIG. 2. Block 204 may direct the analyzer processor 100 to store the received image records in the location 142 of the storage memory 104 shown in FIG. 2. In various embodiments, the received image records may act as a temporally ordered set of image representations of the subject 12.

Block 206 then directs the analyzer processor 100 to determine at least one property representation of the subject 12 based on the function characteristic and the time dependent representation of the subject. In some embodiments, block 206 may direct the analyzer processor 100 to retrieve the set of image records including the image record 280, together acting as a time dependent representation of the received ultrasonic signals, received at block 204 from the location 142 of storage memory 104 and to retrieve the focal depth frequency value stored in the focal depth frequency field 248, acting as a function characteristic, from the location 140 of the storage memory 104. Block 206 may then direct the analyzer processor 100 to determine at least one property representation of the subject based on the set of image records and the focal depth frequency value.

Figure 6:
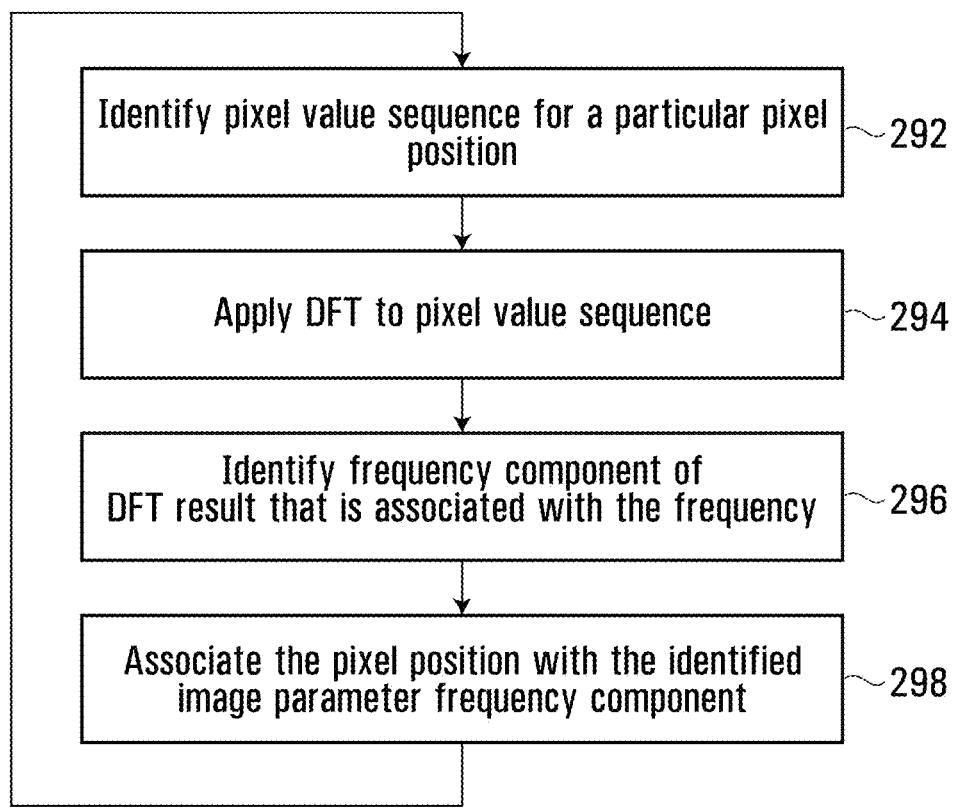
FIG. 6 is a flowchart depicting blocks of code that may be included in the flowchart shown in FIG. 3 in accordance with various embodiments of the present disclosure.

Referring now to FIG. 6, there is shown a flowchart 290 depicting blocks of code for directing the analyzer processor 100 shown in FIG. 2 to perform subject property determining functions in accordance with various embodiments. In various embodiments, the blocks of code included in the flowchart 290 may be included in the block 206 of the flowchart 200 shown in FIG. 5.

Figure 7:
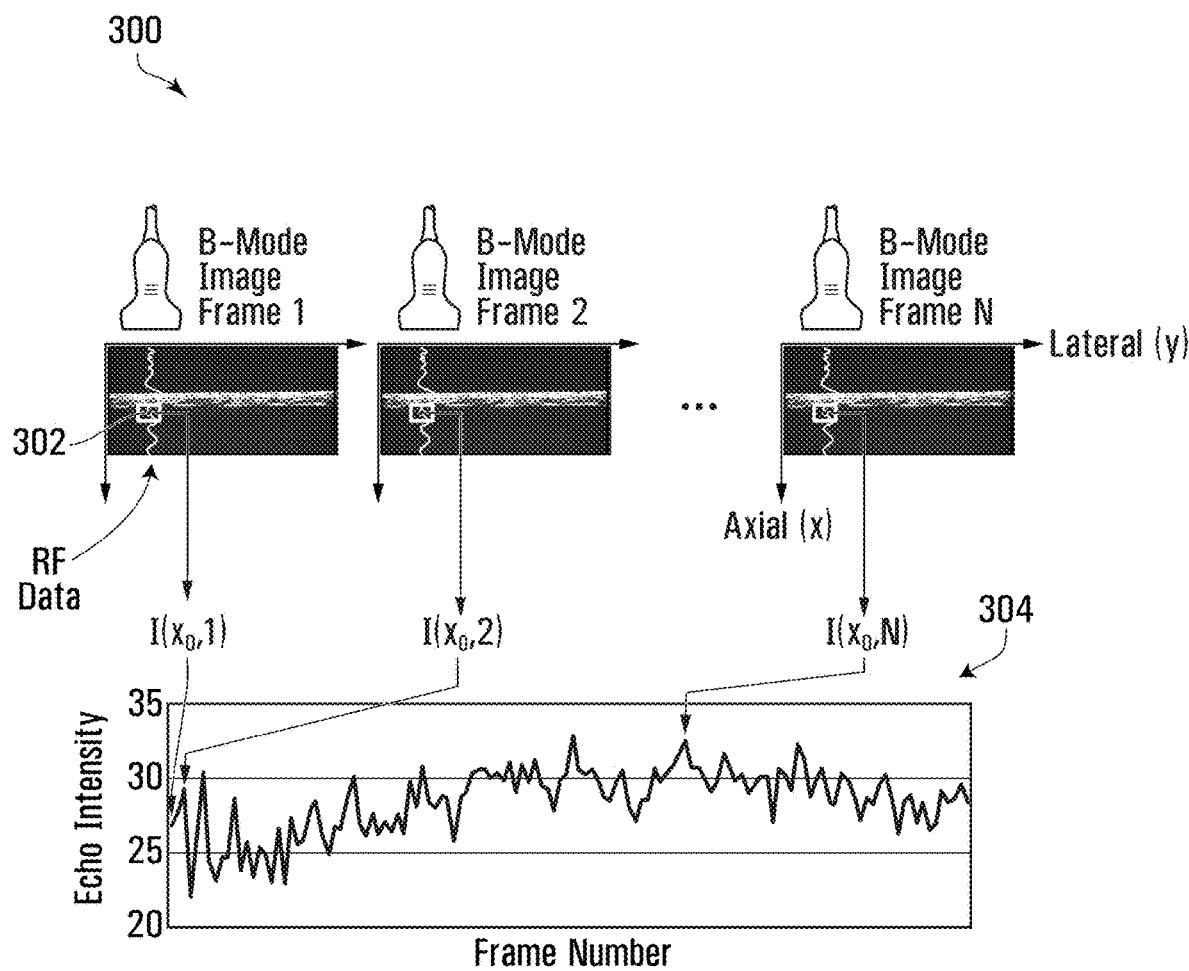
FIG. 7 is a representation of images that may be used in the system shown in FIG. 1 in accordance with various embodiments of the present disclosure.

The flowchart 290 begins with block 292 which directs the analyzer processor 100 to identify a sequence of pixel values for a pixel position in the set of images included in the set of image records stored at the location 142 of the storage memory 104. For example, in some embodiments, block 292 may direct the analyzer processor 100 to read the pixel values for position (0,0) in each image of the set of images and generate a pixel value sequence vector, representing the pixel values for position (0,0). Block 292 may direct the analyzer processor 100 to store the pixel value sequence vector in the location 144 of the storage memory 104. For example, referring to FIG. 7, there is shown a representation of images 300 that may be included in the image records stored in the location 142 of the storage memory 104, in accordance with various embodiments. FIG. 7 shows a representative pixel 302 at a particular position in the images 300, which may correspond to a particular position or location in the subject 12. FIG. 7 shows how the pixel value representing echo intensity or material density 304 associated with the pixel 302 changes over time. Block 292 may direct the analyzer processor 100 to generate and store in the location 144 of the storage memory 104, a pixel value sequence vector representing an echo intensity over time for the first pixel position (0,0).

Block 294 then directs the analyzer processor 100 to apply a discrete Fourier transform (DFT) to the pixel value sequence vector generated at block 292. In some embodiments, block 294 may direct the analyzer processor 100 to apply a DFT normalized to the frame rate of image acquisition and generate a DFT vector from the application of the DFT, the DFT vector including absolute value components of the computed DFT, each of the absolute value components associated with a frequency. Block 294 may direct the analyzer processor 100 to store the DFT vector in the location 146 of the storage memory 104 shown in FIG. 1. In some embodiments, block 294 may direct the analyzer processor 100 to apply a fast Fourier Transform (FFT) to the pixel value sequence vector generated at block 292 to generate the DFT vector.

Referring to FIG. 6, block 296 then directs the analyzer processor 100 to identify from the result of the DFT, a component that is associated with the focal depth frequency value stored in the focal depth frequency field 248 of the ultrasound instruction message 240 shown in FIG. 4. In some embodiments, the identified component may act as an imaging parameter frequency component since it may be associated with the frequency at which the imaging parameter (i.e., the focal depth in some embodiments) varies. In some embodiments, block 296 may direct the analyzer processor 100 to identify a component or value from the DFT vector stored in the location 146 of the storage memory 104 as associated with the focal depth frequency. In various embodiments, block 296 may direct the analyzer processor 100 to apply knowledge of the sampling frequency of the signal or frame rate to determine which component of the DFT vector corresponds to the focal depth frequency. For example, in some embodiments, if the focal depth frequency is f=5.7 Hz, the period for the focal depth function is T=1/f=0.1754 s. In some embodiments, the sampling time may be ts=T/128=0.00137 and the sampling frequency may be Fs=1/ts=729.6 Hz. In various embodiments where 128 frames are used, the second frequency component in FFT corresponds to 1/128*Fs=5.7 Hz. Hence, in such embodiments, the amplitude of the second frequency component corresponds to the focal depth frequency of 5.7 Hz.

Block 298 then directs the analyzer processor 100 to associate the identified component with the pixel position being considered. In some embodiments, on a first execution of block 298, block 298 may direct the analyzer processor 100 to generate a frequency component image and to set a pixel position of the frequency component image corresponding to the pixel position that was considered at block 292 to the component or value identified at block 296 of the flowchart 290. Block 298 may direct the analyzer processor 100 to store the frequency component image in the location 148 of the storage memory 104. In various embodiments in subsequent executions of block 298, block 298 may direct the analyzer processor 100 to modify the frequency component image previously generated and stored in the location 148 of the storage memory 104 to include further pixel values at respective considered pixel positions.

After block 298 has been completed for a particular pixel position, the analyzer processor 100 may be directed to return to block 292 and to consider another pixel position. In various embodiments, blocks 292 to 298 may be repeated for each pixel position included in the images stored in the location 144 of the storage memory 104. Once every pixel position of the images stored in the location 142 of the storage memory 104 has been considered during execution of blocks 292 to 298, the frequency component image stored in the location 148 of the storage memory 104 and each of the pixel values included therein may act as a representation of features or properties of the subject 12. In some embodiments, deviation of pixel values from a mean pixel value may represent an anomaly or probability of an anomaly in the subject 12 at a particular location in the subject. In various embodiments, once every pixel position has been considered, the frequency component image may be visualized as a color map, which shows the imaging parameter frequency component for each pixel position.

Figure 8:
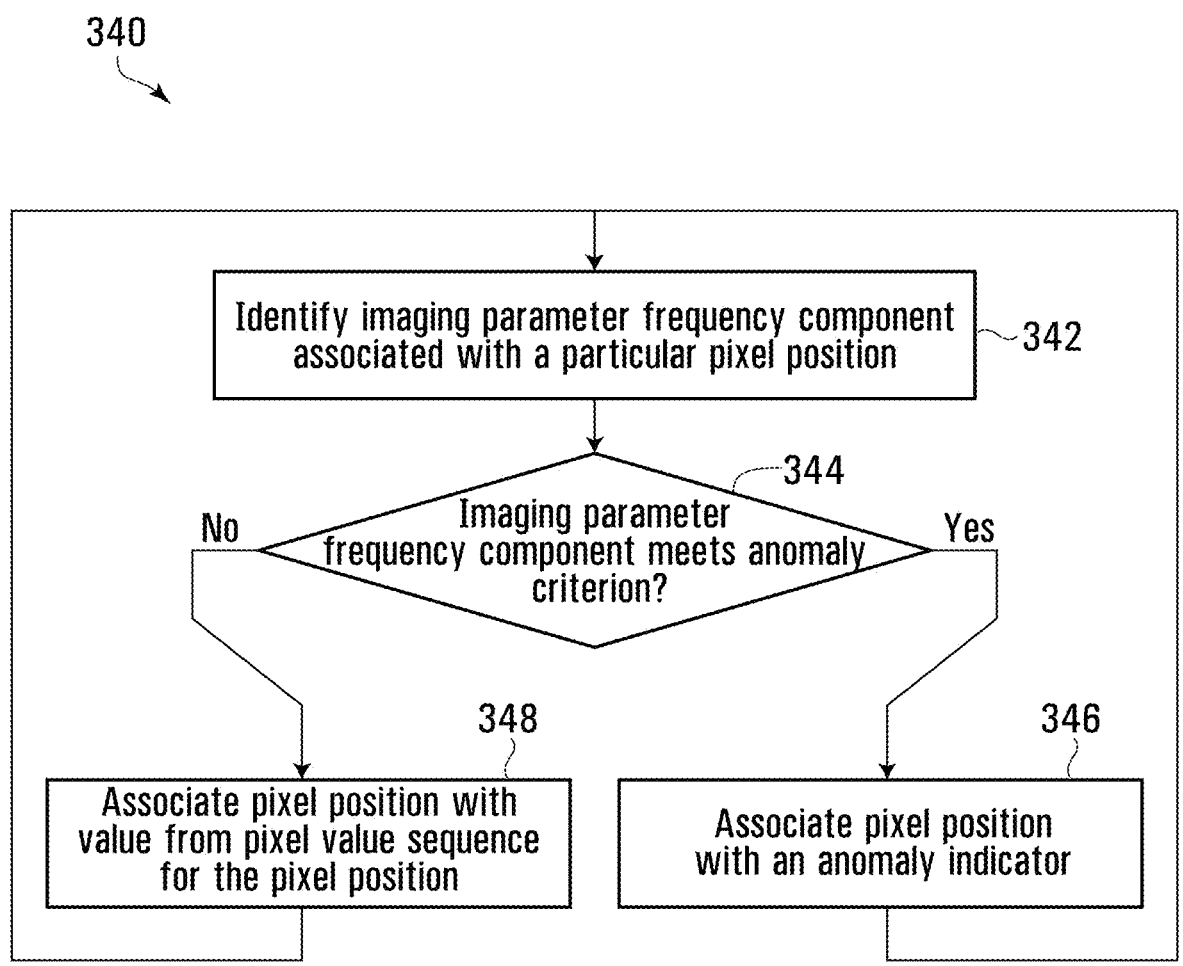
FIG. 8 is a flowchart depicting blocks of code that may be included in the flowchart shown in FIG. 3 in accordance with various embodiments of the present disclosure.

In some embodiments, block 206 may direct the analyzer processor 100 to, for each of the imaging parameter frequency components determined, apply anomaly criteria to the determined component to determine whether the imaging parameter frequency component indicates presence of an anomaly in the subject 12. Referring now to FIG. 8, there is shown a flowchart 340 depicting blocks of code for directing the analyzer processor 100 shown in FIG. 2 to perform anomaly detection functions in accordance with various embodiments. In various embodiments, the blocks of code included in the flowchart 340 may be included in the block 206 of the flowchart 200 shown in FIG. 3 and may be executed after the blocks of code included in the flowchart 290 shown in FIG. 6 have been executed.

The flowchart 340 begins with block 342 which directs the analyzer processor 100 to identify an imaging parameter frequency component associated with a particular pixel position. In some embodiments, block 342 may direct the analyzer processor 100 to read the frequency component image from the location 148 of the storage memory 104 and to identify a first imaging parameter frequency component of the frequency component image associated with a first pixel position in the frequency component image.

Block 344 then directs the analyzer processor 100 to apply at least one anomaly criterion to the identified imaging parameter frequency component to determine whether the imaging parameter frequency component indicates presence of an anomaly in the subject. In some embodiments, expected values for the imaging parameter frequency components may be within a predetermined normal range and so block 344 may direct the analyzer processor 100 to determine whether the imaging parameter frequency component is outside of a predetermined normal range.

For example, in some embodiments, an anomaly range record 360 shown in FIG. 9 may have been previously determined or provided and may be stored in the location 150 of the storage memory 104. Referring to FIG. 9, in various embodiments, the anomaly range record 360 includes a minimum field 362 and a maximum field 364 for storing values defining the predetermined normal range. Block 344 may direct the analyzer processor 100 to compare the first imaging parameter frequency component to the values from the minimum and maximum fields 362 and 364 of the anomaly range record 360 and to determine whether the first imaging parameter frequency component is less than the value stored in the minimum field 362 or greater than the value stored in the maximum field 364. In some embodiments, there may be no minimum value and so the minimum field 362 may be omitted. In such embodiments, block 344 may direct the analyzer processor 100 to determine whether the first imaging parameter frequency component is greater than the value stored in the maximum field 364. In some embodiments, the minimum and maximum values may have been previously determined by scanning one or more samples similar to the subject 12 but without anomalies and determining a range of pixel values for frequency component images generated from the samples.

If at block 344 it is determined that the at least one anomaly criterion is met and the imaging parameter frequency component indicates presence of an anomaly in the subject 12, the analyzer processor is directed to block 346. For example, if at block 344 it is determined that the first imaging parameter frequency component is greater than the value stored in the maximum field 364, block 344 may direct the analyzer processor 100 to proceed to block 346.

Block 346 directs the analyzer processor 100 to associate the pixel position with an anomaly indicator. In some embodiments, block 346 may direct the analyzer processor 100 to set the pixel position identified at block 342 of an anomaly indicating image to an anomaly indicator value. In various embodiments, the anomaly indicating image may be stored in the location 152 of the storage memory 104. In some embodiments, block 346 may direct the analyzer processor 100 to set the pixel position to an anomaly indicator value that represents an indicator color, such as, for example, red. In various embodiments, by associating the pixel position with an anomaly indicator, anomalies in the imaging parameter frequency components may be easily identified.

If at block 344 it is determined that the at least one anomaly criterion is not met and the imaging parameter frequency component does not indicate presence of an anomaly in the subject 12, the analyzer processor is directed to block 348. For example, if at block 344 it is determined that the first imaging parameter frequency component is less than the value stored in the maximum field 364 and greater than the value stored in the minimum field 362, block 344 may direct the analyzer processor 100 to proceed to block 348.

Block 348 may direct the analyzer processor 100 to associate the pixel position with a value that indicates that there is not an anomaly at the pixel position. In some embodiments, block 348 may direct the analyzer processor 100 to associate the pixel position with a value that represents the color blue, for example.

After either block 346 or 348 has been executed, the analyzer processor 100 is directed to return to block 342 and to consider another pixel position of the frequency component image retrieved from the location 148 of the storage memory 104. In various embodiments, blocks 342, 344, and 346 or 348 may be executed for each pixel position in the frequency component image until a complete anomaly indicating image is stored in the location 152 of the storage memory 104.

Figure 10:
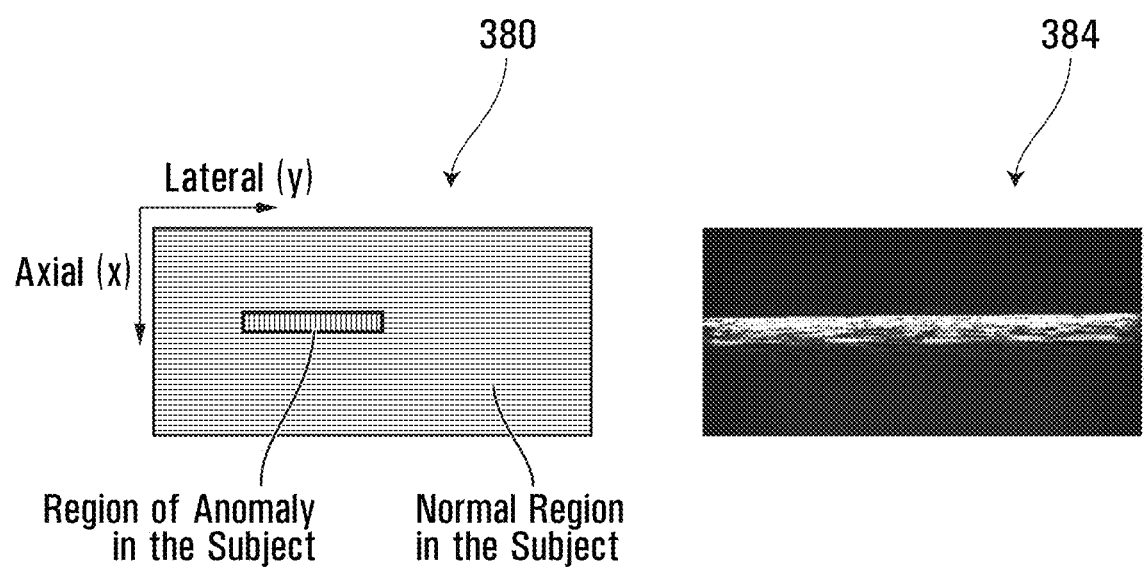
FIG. 10 is a representation of an exemplary anomaly indicating image and an image that may be used in the system shown in FIG. 1 in accordance with various embodiments of the present disclosure.

Referring to FIG. 10, a representation of an exemplary anomaly indicating image 380 that may be stored in the location 152 of the storage memory 104 after flowchart 340 has been executed is shown beside an image 384 included in one of the image records, for reference. Referring to FIG. 10, the anomaly indicating image 380 includes a region of anomaly which is indicated by the color red (represented in FIG. 10 by vertical line hatching), and a normal region which is indicated by the color blue (represented in FIG. 10 by horizontal line hatching).

In various embodiments, the anomaly indicating image 380 stored in the location 152 of the storage memory 104 and each of the pixel values included in the anomaly indicating image may act as representations of features or properties of the subject 12.

Referring to FIG. 3, in some embodiments, block 206 may direct the analyzer processor 100 to determine a representative value from the frequency component image stored in the location 148 of the storage memory 104. For example, in some embodiments block 206 may direct the analyzer processor 100 to determine a median pixel value from the frequency component image and to store the median pixel value in the location 148 of the storage memory 104. In various embodiments, the median pixel value may be representative of a level of porosity in the subject 12. For example, in some embodiments, as the median pixel value increases, this may indicate a higher porosity of the subject 12.

Figure 11:
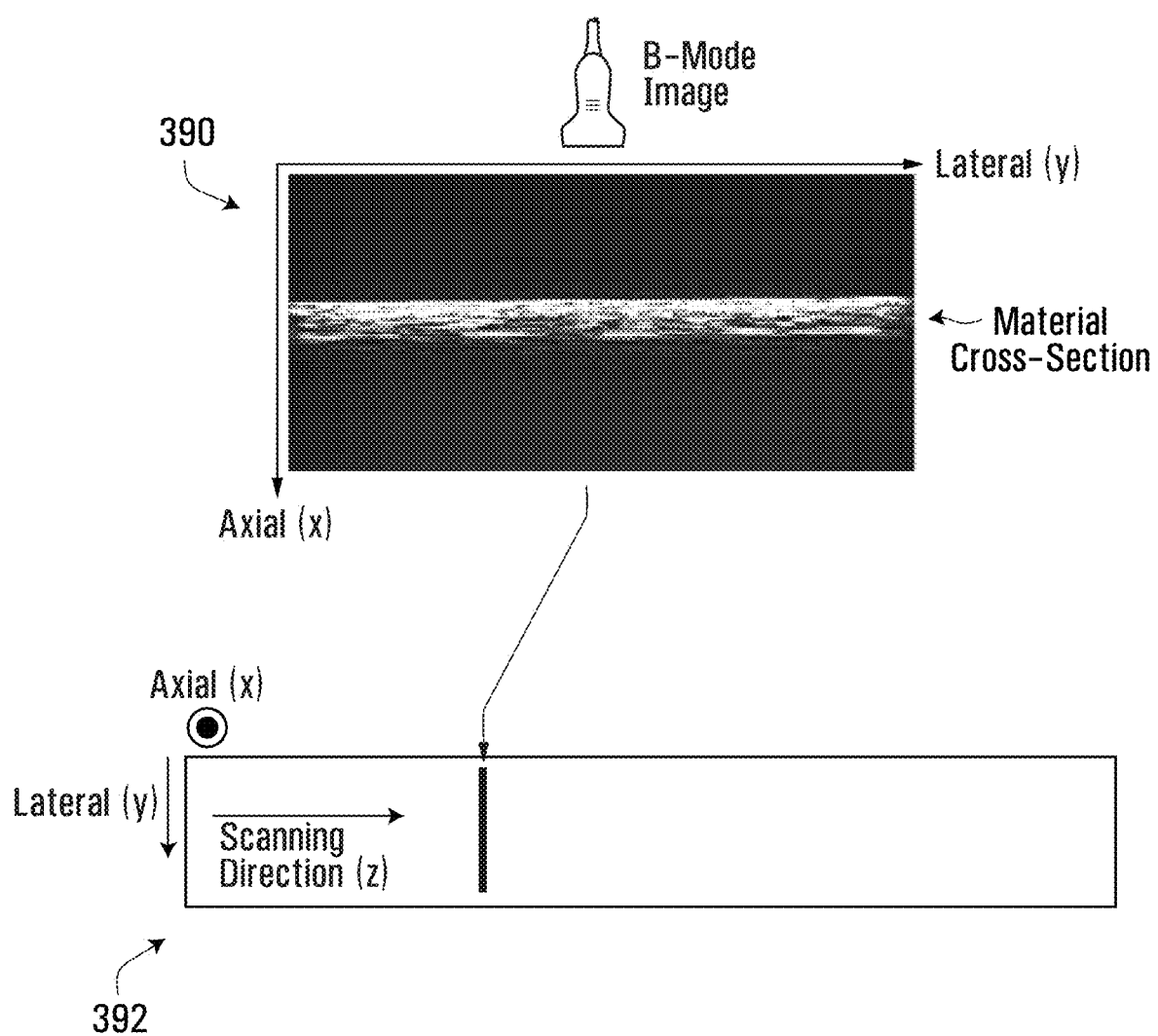
FIG. 11 is a representation of how an image of the system may fit as a plane of voxels in a larger 3D representation in FIG. 1 in accordance with various embodiments of the present disclosure

In some embodiments, blocks 202, 204, and 206 of the flowchart 200 may be executed for a plurality of positions on the subject 12, such that the 3-dimensional subject 12 may be characterized at a plurality of planes. For example, in some embodiments, the system 10 may include a Y-Z stage and the analyzer 14 may be configured to execute blocks 202, 204, and 206 of the flowchart 200 shown in FIG. 3 in a first Z position. The system 10 may then move the subject 12 using the Y-Z stage relative to the transducer 20 and then the analyzer 14 may execute blocks 202, 204, and 206 in the next Z-position. For example, in some embodiments, the subject 12 may move about 1 mm at a time. The entire movement procedure may be automated such that the subject 12 moves with increments of 1 mm representing a 1 mm scanning resolution across the entire subject. Accordingly, in various embodiments, the pixels discussed herein may act as a plane of voxels in a larger 3D representation of the subject. FIG. 11 shows how an image 390 included in the image records stored in the location 142 of the storage memory 104 may fit as a plane of voxels within a 3D representation 392 of properties of the subject 12. In various embodiments, the frequency component images stored in the location 148 of the storage memory 104 and/or the anomaly indicating images stored in the location 152 of the storage memory 104 may similarly together form respective 3D representations of properties of the subject 12.

In some embodiments, the ultrasound image data stored in the location 142 may be collected in various ways. For example, in some embodiments, the ultrasound image data stored in the location 142 of the storage memory 104 may be collected over equally-sized Regions of Interests (ROI), where the width of each ROI is the half of the probe width (e.g., 1.9 cm) and its depth is equal to the sample's thickness. For each imaging plane, analysis may be performed for 2 ROIs that cover the entire cross section of the subject 12.

Referring back to FIG. 3, block 208 directs the analyzer processor 100 to produce signals representing the at least one property representation determined at block 206 to facilitate analysis of the subject 12. In some embodiments, block 208 may direct the analyzer processor 100 to produce signals representing one or more of the frequency component images stored in the location 148 for causing the display 18 shown in FIG. 1 to display a representation of the frequency component images. For example, in some embodiments, a 3D representation of the frequency component images may be displayed. In various embodiments, a user or quality assurance specialist viewing the display 18 may be able to use the display 18 showing the frequency component images to determine whether the subject 12 can be used for a desired application. For example, in various embodiments, the user may determine that the frequency component images include too many high and/or low pixel values that are different from an average or normal pixel value and that therefore the subject 12 has too many imperfections or too high of a porosity to be used in the intended application.

In some embodiments, block 208 may direct the analyzer processor 100 to produce signals representing the median pixel value stored in the location 148 of the storage memory 104 for one or more of the frequency component images, for causing the display 18 shown in FIG. 1 to display a representation of the median pixel value. In various embodiments, a user or quality assurance specialist viewing the display 18 may be able to use the display 18 showing the median pixel values to determine whether the subject 12 can be used for a desired application. For example, in various embodiments, the user may determine that the median pixel values are too high or too low and therefore has too many imperfections or too high of a level of porosity for the intended application.

In some embodiments, block 208 may direct the analyzer processor 100 to produce signals representing one or more of the anomaly indicating images stored in the location 152 for causing the display 18 to display a representation of the one or more anomaly indicating images. For example, in some embodiments, block 208 may direct the analyzer processor 100 to produce signals representing a plurality of anomaly indicating images such that a 3D view or a top down view of one or more cross sections taken at a pixel position on the x axis may be displayed by the display 18. In various embodiments, a user or quality assurance specialist viewing the display 18 may be able to use the display 18 showing the anomaly indicating images to determine whether the subject 12 can be used for a desired application. For example, in various embodiments, the user may determine that the anomaly indicating image includes too many pixel positions that are associated with anomaly indicator values and that therefore the subject 12 has too many imperfections to be used in an aerospace application.

Various Embodiments

In some embodiments, the variable imaging parameter function may be representable by more than one function characteristic, which may be used to determine the at least one property representation of the subject 12. For example, in some embodiments, a focal depth function may be used that includes more than one periodic function, each having a different frequency. Accordingly, in various embodiments, an ultrasound instruction message 400 as shown in FIG. 12 may be stored in the location 140 of the storage memory 104 and used generally as described above having regard to the ultrasound instruction message 240 shown in FIG. 4.

Referring to FIG. 12, the ultrasound instruction message 400 includes a focal depth function definition 402 that includes more than one periodic function, such that the focal depth of the ultrasonic signals transmitted to the subject 12 by the ultrasound machine 16 may vary according to more than one periodic function. Accordingly, referring to FIG. 12, in some embodiments, the focal depth function definition 402 may define a focal depth as follows:

$$\text{Focal depth (in microns)} = D + A \sin(2\pi f_1 \cdot i) + B \sin(2\pi f_2 \cdot i)$$

where i is the frame index number for each transmitted ultrasonic signal.

Accordingly, in various embodiments, the focal depth function may include a first periodic function $A^*\sin(2pi^*f_1^*i)$ where $f_1$ is a first focal depth frequency and a second periodic function $B^*\sin(2pi^*f_2^*i)$ where $f_2$ is a second focal depth frequency, wherein $f_2$ is different from $f_1$. In such embodiments, the values for $f_1$ and $f_2$ may each act as respective function characteristics for the focal depth function.

In various embodiments, where the ultrasound instruction message 400 is transmitted to the ultrasound machine 16, block 296 of the flowchart 290 shown in FIG. 6 may direct the analyzer processor 100 to identify first and second frequency components of the DFT result, the first and second frequency components associated with the first and second focal depth frequencies. In various embodiments, block 298 of the flowchart 290 shown in FIG. 6 may direct the analyzer processor 100 to determine a difference between the first and second frequency components and to associate the pixel position with the difference between the identified first and second frequency components. Block 298 may, for example, direct the analyzer processor 100 to generate a frequency component differentiator image which includes a representation of the difference between frequency component values associated with each pixel position. In various embodiments, the generated frequency component differentiator image may act as a property representation of the subject.

In various embodiments, alternative or additional imaging parameters and imaging parameter functions may be utilized generally as described herein regarding the focal depth acting as an imaging parameter and the focal depth function acting as an imaging parameter function defining how the focal depth varies over time. For example, in some embodiments imaging parameters that may be treated generally as described herein regarding the focal depth, may include focal depth, f-number, apodization window, time gain compensation (TGC), dynamic range, number of active elements, centre frequency of the transducer, shape of the transmitted signal, direction of the transmitted signal (which may be changed using beam steering, for example), length of the transmitted signal, and/or another imaging parameter that affects the point spread function of the imaging system.

For example, in some embodiments, an ultrasound instruction message 420 as shown in FIG. 13 may be stored in the location 140 of the storage memory 104 and used generally as described above having regard to the ultrasound instruction message 240 shown in FIG. 4, except the ultrasound instruction message 420 may cause the ultrasound machine 16 to vary a centre frequency of the transmitted signals based on the ultrasound instruction message 420. Referring to FIG. 13, the ultrasound instruction message 420 includes a centre frequency function definition 422 for defining the centre frequency in Hz of the ultrasonic signals to be transmitted to the subject 12 by the ultrasound machine 16, such that the centre frequency may vary according to the centre frequency function definition 422.

In some embodiments, the centre frequency function may be used on its own generally as described above for the focal depth function. However, in other embodiments, the centre frequency function may be used in conjunction with varying of another imaging parameter, such as, for example, the focal depth. Accordingly, in various embodiments, the flowcharts 200 and 290 shown in FIGS. 3 and 6 may be executed first as described above using the ultrasound instruction message 240 shown in FIG. 5 and then the flowcharts 200 and 290 may be executed generally as described above but using the ultrasound instruction message 420 shown in FIG. 13.

Accordingly, in various embodiments, a focal depth frequency component image and a centre frequency component image for the same planar position in the subject 12 may thus be stored in the location 148 of the storage memory 104. In some embodiments, when both the focal depth frequency component image and the centre frequency component image are stored in the location 148 of the storage memory 104, block 206 may direct the analyzer processor 100 to determine, for each pixel position in the images stored in the location 148 of the storage memory 104, a difference between the pixel values of the focal depth frequency component image and the centre frequency component image. Block 206 may direct the analyzer processor 100 to generate and store a differentiator image representing the differences in pixel values at each pixel position. The differentiator image may be stored in the location 154 of the storage memory 104, for example.

In some embodiments, block 208 may direct the analyzer processor 100 to produce signals representing the differentiator image stored in the location 154 for causing the display 18 to display a representation of the differentiator image. In various embodiments, a user viewing the differentiator image may be able to determine properties of the subject 12 in view of the differentiator image. For example, in some embodiments, the user may be able to determine a material type from the displayed differentiator image.

In some embodiments, a differentiator image may be generated as described above, but using two different functions for the same imaging parameter. For example, in some embodiments, an ultrasound instruction message 440 as shown in FIG. 14 may be used as described above instead of the ultrasound instruction message 420 shown in FIG. 13.

In some embodiments block 208 of the flowchart 200 shown in FIG. 3 may direct the analyzer processor 100 to produce signals representing the at least one property representation of the subject to facilitate analysis of the subject 12 using a neural network. For example, in some embodiments, block 208 may direct the analyzer processor 100 to use the frequency component images and/or the anomaly indicating images stored in the location 148 of the storage memory 104 as inputs into a neural network for analyzing the images.

In some embodiments, block 208 of the flowchart 200 shown in FIG. 3 may direct the analyzer processor 100 to transmit signals representing the at least one property representation of the subject to facilitate analysis at another computer of the subject 12. For example, in some embodiments, the I/O interface 112 may include a network interface and block 208 may direct the analyzer processor 100 to transmit representations of frequency component images and/or the anomaly indicating images stored in the location 148 of the storage memory 104 to another computer via the network interface to facilitate analysis at the other computer.

In some embodiments, the ultrasound machine 16 may include 3D transducers or circular, array transducers which may not require any motion to scan in 3D. In some embodiments, the ultrasound machine 16 may include more than one transducer, such as, for example, one sending a signal from one side and one receiving a signal from the other side.

In various embodiments alternative or additional imaging parameter functions or focal depth functions may be used. For example, in some embodiments, a focal depth function that is not periodic may be used.

In various embodiments, block 206 of the flowchart 200 shown in FIG. 3 may direct the analyzer processor 100 to, instead of applying the DFT, convolve the focal depth function with the time dependent subject representation (e.g., by convolving the focal depth function with the pixel value sequence vectors) to determine convolution values that may be included in a convolution image which may be treated generally similarly to the frequency component image described herein.

In various embodiments, the shape of the focal depth function may include any varying function, such as, for example, a step or a triangle, or a sequence of pulses of varying length or amplitude, or another varying function, such as, for example a function that includes randomly varying elements.

In some embodiments, the focal depth function may result in a sequence of ultrasonic or transmit signals being produced that vary the focal point sinusoidally according to an index or time value. However, in some embodiments, the order of firing or transmitting of that sequence of signals to the subject 12 may be scrambled randomly in time, as each backscattered data frame may be considered independent of the subsequent data frame. In such embodiments, block 206 may direct the analyzer processor 100 to first re-sort the received image frames and then to perform an analysis generally as described herein.

While various embodiments described herein have been described in connection with the subject 12 being made of a composite material, in various embodiments, the system 10 may facilitate ultrasonic characterization of other subjects for which accurate characterization is required. For example, in some embodiments, the system 10 may be configured to facilitate ultrasonic characterization in biomedical applications, such as for in vivo and ex vivo characterization of biological material, such as, for example, for tissue or organ analysis. For example, in some embodiments, the system 10 may be used to detect cancer, such as, for example prostate cancer and/or breast cancer.

While various embodiments described herein involved the use of a DFT or FFT and selection of components of a result of the DFT or FFT, in various embodiments alternative or additional processing of the time dependent representation of the subject may be used. For example, in some embodiments, block 206 may direct the analyzer processor 100 to more generally apply a band-pass filter to the time dependent representation of the subject 12 received at block 204, wherein the band-pass filter is configured to pass the focal depth frequency.

In various embodiments, block 206 may process the time dependent representation of the subject 12 using additional or alternative analyses compared to the DFT described above, which may be based on time, frequency, amplitude, statistical, stochastic or a combination thereof. For example, in some embodiments, block 206 may direct the analyzer processor 100 to use a band-pass filter such as a finite impulse response (FIR) filter to filter the time dependent representation, and to use a property of the filtered result, such as the power of the filtered result or its amplitude, for example, to facilitate ultrasonic analysis of a subject. For example, in some embodiments, the power of the filtered result or its amplitude may act as a representation of at least one property of the subject 12. In some embodiments, the design of the FIR filter may be informed from the variable imaging parameter function. In some embodiments, the FIR filter may have a passband centered around a frequency of the variable imaging parameter function. For example, if the focal depth variation frequency is 10 Hz, then the FIR filter may be implemented as a 10 Hz bandpass filter.

In some embodiments, block 206 of the flowchart 200 shown in FIG. 3 may direct the analyzer processor 100 to input the time dependent representation of the subject 12 and the function characteristic into a neural network, the neural network having been trained/configured to determine whether the subject 12 has a defect based on the input time dependent representation of the subject 12 and the function characteristic. In some embodiments, the neural network may act as a classifier and may output a determined probability or likelihood that there is a defect in the subject 12. In such embodiments, the determined probability that there is a defect in the subject 12 may act as the at least one property representation of the subject.

In various embodiments, block 208 may then direct the analyzer processor 100 to, if it is determined by the neural network that the subject has a high probability of a defect (e.g., by determining whether the probability of a defect is higher than a threshold probability), produce signals for causing an alert to be provided for a user of the analyzer 14. For example, in some embodiments, block 208 may direct the analyzer processor 100 to, produce signals for causing the display 18 to provide an alert noting that the subject 12 likely has a defect.

In some embodiments, block 206 may direct the analyzer processor 100 to use a deep neural network that is trained to perform DFT and perform an analysis on the result. In some embodiments, block 206 may direct the analyzer processor 100 to use a neural network that is trained to extract a specific frequency component (corresponding to the focal depth frequency, for example) from each of the pixel value sequences without needing to use a full DFT calculation for all frequency components.

While the system 10 shown in FIG. 1 includes the ultrasound machine 16 which is shown pictorially as a standard cart-based ultrasound machine, in various embodiments, the system 10 may be implemented in alternative environments, such as, for example, in an assembly line or in a handheld device for use in the field.

Figure 15:
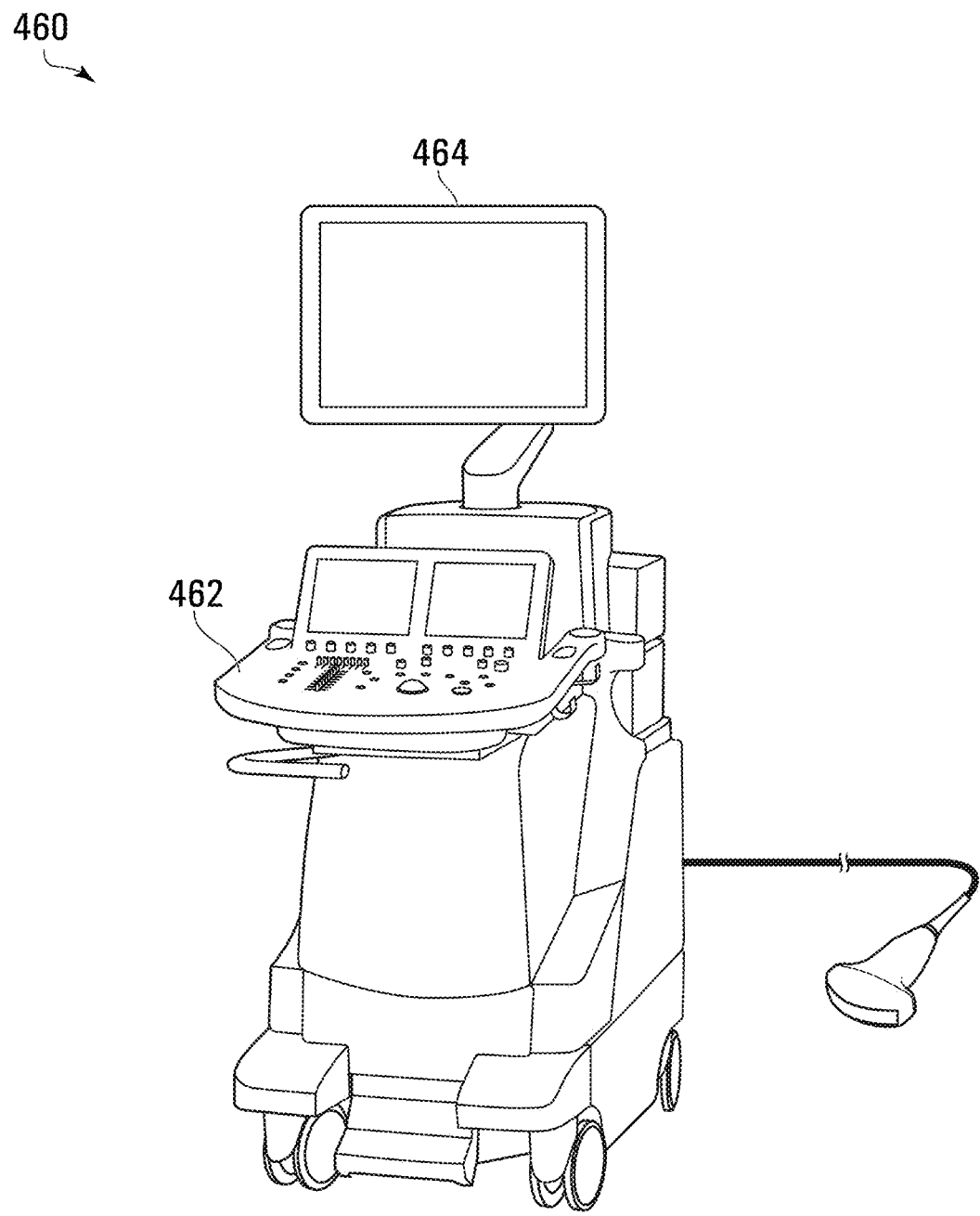
FIG. 15 is a schematic view of a system for facilitating ultrasonic analysis of a subject, according to various embodiments of the present disclosure.

In various embodiments, a system 460 shown in FIG. 15 that functions generally similarly to the system 10 described herein and shown in FIG. 1 may include an ultrasound machine 462 that incorporates an analyzer within the ultrasound machine 462, the analyzer having generally similar functionality to the analyzer 14 described herein. For example, in various embodiments, a single processor circuit included in the ultrasound 462 may implement functionality of both the ultrasound machine 16 and the analyzer 14 described herein. In various embodiments a display 464 of the system 460 may be used generally as described above regarding the display 18 of the system 10 shown in FIG. 1.

In various embodiments, any or all of the ultrasound machine 16, transducer 20, analyzer 14 and/or display 18 may be implemented as a combined single device that incorporates any or all of the functionality described herein.

In various embodiments, time dependent representations and/or functions described herein may be merely variable over time and may, in some embodiments, include random elements.

While specific embodiments of the present disclosure have been described and illustrated, such embodiments should be considered illustrative of the present disclosure only and not as limiting the present disclosure as construed in accordance with the accompanying claims.

In this disclosure, one or more publications, patents, and/or patent applications may be incorporated by reference. However, such material is only incorporated to the extent that no conflict exists between the incorporated material and the statements and drawings set forth herein. In the event of any such conflict, including any conflict in terminology, the present disclosure is controlling.

The invention claimed is:

1. A method of facilitating ultrasonic analysis of a subject, the method comprising:
   producing signals for causing a set of outgoing ultrasonic signals to be transmitted to the subject, wherein the set of outgoing ultrasonic signals is defined at least in part by a variable imaging parameter that varies over time in accordance with a variable imaging parameter function, the variable imaging parameter function represented or representable at least in part by a function characteristic;
   receiving signals representing a time dependent representation of the subject generated from a set of received ultrasonic signals scattered by the subject;
   determining at least one property representation of the subject based on the function characteristic and the time dependent representation of the subject; and
   producing signals representing the at least one property representation of the subject to facilitate analysis of the subject.

2. The method of claim 1 wherein the set of outgoing ultrasonic signals is a temporally ordered set of outgoing ultrasonic signals and wherein the variable imaging parameter varies over the temporally ordered set of outgoing ultrasonic signals.

3. The method of claim 1 wherein the set of outgoing ultrasonic signals includes at least one ultrasonic beam and wherein producing the signals for causing the set of outgoing ultrasonic signals to be transmitted to the subject comprises producing signals for causing the at least one ultrasonic beam to be transmitted to the subject, said at least one ultrasonic beam defined at least in part by the variable imaging parameter.

4. The method of claim 3 wherein the variable imaging parameter is a focal depth of the at least one ultrasonic beam and wherein producing the signals for causing the at least one ultrasonic beam to be transmitted to the subject comprises producing signals for causing the focal depth of the at least one ultrasonic beam to vary over time according to the variable imaging parameter function.

5. The method of claim 1 wherein the variable imaging parameter function includes a periodic function that varies over time at an imaging parameter frequency and wherein the function characteristic includes the imaging parameter frequency.

6. The method of claim 5 wherein determining the at least one property representation of the subject comprises applying a band-pass filter to the time dependent representation of the subject, the band-pass filter configured to pass the imaging parameter frequency.

7. The method of claim 5 wherein determining the at least one property representation of the subject comprises applying a discrete Fourier transform to the time dependent representation of the subject to determine one or more imaging parameter frequency components, each of the one or more imaging parameter frequency components associated with the imaging parameter frequency.

8. The method of claim 7 further comprising, for each of the one or more imaging parameter frequency components, applying at least one anomaly criterion to the imaging parameter frequency component to determine whether the imaging parameter frequency component indicates presence of an anomaly in the subject.

9. The method of claim 8 wherein applying the at least one anomaly criterion comprises determining whether the imaging parameter frequency component is outside of a predetermined normal range.

10. The method of claim 9 wherein producing the signals representing the at least one property representation of the subject comprises producing signals for causing at least one display to display a representation of the subject including indicators identifying the one or more imaging parameter frequency components determined to be outside of the predetermined normal range.

11. The method of claim 7 wherein producing the signals representing the at least one property representation of the subject comprises producing signals for causing at least one display to display a representation of the one or more imaging parameter frequency components.

12. The method of claim 5 wherein:
the periodic function is a first periodic function and the imaging parameter frequency is a first imaging parameter frequency;
the variable imaging parameter function includes a second periodic function that varies over time at a second imaging parameter frequency, different from the first imaging parameter frequency, such that the variable imaging parameter function is represented or representable at least in part by the second imaging parameter frequency; and
determining the at least one property representation of the subject based on the function characteristic and the time dependent representation of the subject comprises determining the at least one property representation of the subject based on the first imaging parameter frequency, the second imaging parameter frequency, and the time dependent representation of the subject.

13. The method of claim 1 wherein:
the set of outgoing ultrasonic signals is a first set of outgoing ultrasonic signals;
the variable imaging parameter is a first variable imaging parameter;
the variable imaging parameter function is a first variable imaging parameter function;
the function characteristic is a first function characteristic;
the method further comprises:
produce signals for causing a second set of outgoing ultrasonic signals to be transmitted to the subject, wherein the second set of outgoing ultrasonic signals is defined at least in part by a second variable imaging parameter that varies over time in accordance with a second variable imaging parameter function, the second variable imaging parameter function represented or representable at least in part by a second function characteristic; and
receiving signals representing a second time dependent representation of the subject generated from a second set of received ultrasonic signals scattered by the subject; and
determining the at least one property representation of the subject comprises determining the at least one property representation of the subject based on the first function characteristic, the second function characteristic, and the time dependent representation of the subject.

14. The method of claim 1 wherein the subject is a composite material.

15. A system for facilitating ultrasonic analysis of a subject, the system comprising at least one processor configured to:
produce signals for causing a set of outgoing ultrasonic signals to be transmitted to the subject, wherein the set of outgoing ultrasonic signals is defined at least in part by a variable imaging parameter that varies over time in accordance with a variable imaging parameter function, the variable imaging parameter function represented or representable at least in part by a function characteristic;
receive signals representing a time dependent representation of the subject generated from a set of received ultrasonic signals scattered by the subject;
determine at least one property representation of the subject based on the function characteristic and the time dependent representation of the subject; and
produce signals representing the at least one property representation of the subject to facilitate analysis of the subject.

16. A non-transitory computer readable medium having stored thereon codes which when executed by at least one processor cause the at least one processor to:
produce signals for causing a set of outgoing ultrasonic signals to be transmitted to the subject, wherein the set of outgoing ultrasonic signals is defined at least in part by a variable imaging parameter that varies over time in accordance with a variable imaging parameter function, the variable imaging parameter function represented or representable at least in part by a function characteristic;
receive signals representing a time dependent representation of the subject generated from a set of received ultrasonic signals scattered by the subject;
determine at least one property representation of the subject based on the function characteristic and the time dependent representation of the subject; and
produce signals representing the at least one property representation of the subject to facilitate analysis of the subject.

* * * * *